United States Patent [19]
Deno et al.

[11] B 3,993,550
[45] Nov. 23, 1976

[54] PHOTOCHLORINATION OF ALKANOLS

[75] Inventors: Norman C. Deno, State College, Pa.; Harry J. Spinelli, Newark, Del.

[73] Assignee: Research Corporation, New York, N.Y.

[22] Filed: Feb. 18, 1975

[21] Appl. No.: 550,744

[44] Published under the second Trial Voluntary Protest Program on February 17, 1976 as document No. B 550,744.

[52] U.S. Cl. .......................................... 204/158 HA
[51] Int. Cl.$^2$ ............................................. B01J 1/10
[58] Field of Search ............................ 204/158 HA

[56] References Cited
UNITED STATES PATENTS
3,463,826  8/1969  Richtzenhain .............. 204/158 HA

*Primary Examiner*—Howard S. Williams
*Attorney, Agent, or Firm*—Cooper, Dunham, Clark, Griffin & Moran

[57] ABSTRACT

The photochlorination of alkanols, $C_4$ and higher, is advantageously carried out in an aqueous buffered solvent whereby chlorination can predominate over oxidation. The photochlorination of cyclopentanol in an aqueous acetate buffer at a pH of about 5 forms 5-chloropentanal quantitatively.

23 Claims, No Drawings

PHOTOCHLORINATION OF ALKANOLS

This invention relates to chlorination. More particularly, this invention relates to the photochlorination of alkanols, including cycloalkanols.

This invention is based, at least in part, on work supported by a grant from the National Science Foundation.

It has previously been reported, see M. L. Poutsma, "Methods in Free-Radical Chemistry," Vol. I, page 137, Marcel Dekker, N. Y. (1969), that "alcohols react rapidly with chlorine by a series of steps which ultimately lead to oxidation and formation of carbonyl compounds and chlorinated carbonyl compounds and radical chlorination is not a generally useful route to chloro alcohols." Reports on the photochlorination of ethanol and 1-propanol tend to support this view, see O. W. Cass U.S. Patent 2,478,152; C. A. 44, 167 (1950) and A. Brocket, Ann. Chim. (Paris), 10, 338 (1897) and L. Moelants, Bull. Soc. Chim. Belg., 52, 55 (1943).

It is an object of this invention to provide an improved process for the photochlorination of $C_4$ and higher alkanols.

Another object of this invention is to provide a process for the chlorination, particularly the photochlorination, of alkanols having a carbon chain length and a hydroxy substitution such that the alkanol is capable of δ-chlorination whereby the alkanol undergoes δ-chlorination.

How these and other objects of this invention are achieved will become apparent in the light of the accompanying disclosure. In at least one embodiment of the practices of this invention, at least one of the foregoing objects will be achieved.

It has been discovered that primary and secondary alkanols can be photochlorinated with the substantial reduction, even elimination, of competing reactions, such as oxidation and the formation of carbonyl compounds, by protecting the hydroxyl group of the alkanol by protonation. More particularly, it has been discovered that photochlorination of alkanols is carried out with improved results and particularly with respect to the selectivity of the chlorination by reacting a $C_4$ or higher alkanol in an aqueous buffered solvent with chlorine while irradiating the resulting reaction mixture. Where the $C_4$ and higher alkanol has a chain length and hydroxyl group substitution so as to permit δ-chlorination, δ-chlorination occurs.

In the practices of this invention, the aqueous buffered solvent employed may be buffered to a pH in the range from about 4 to about 9, preferably slightly acidic, such as buffered to a pH in the range 4–6, more or less. A particularly useful aqueous buffered solvent is an aqueous acetate buffer having a pH of about 5.

In effecting the photochlorination reaction in accordance with this invention, the reaction mixture comprising the alkanol undergoing chlorination and the aqueous buffered solvent is maintained in the liquid phase with agitation and preferably at a temperature in the range 10°–35°C., more or less, preferably in the range 15°–25°C. or at ambient temperature. Also, the photochlorination reaction in accordance with this invention is carried out in the substantial absence of oxygen. This condition may be achieved by maintaining the reaction mixture, after purging with gaseous nitrogen to displace any air or oxygen from the reaction mixture, under a blanket or in an atmosphere of gaseous nitrogen.

The practices of this invention are applicable to the photochlorination of $C_4$ and higher molecular weight or longer chain length alkanols, broadly, including cycloalkanols. The alkanols which are capable of undergoing photochlorination in accordance with the practices of this invention with the substantial absence or reduction of competing reactions, such as oxidation, include both the corresponding primary and secondary alkanols. Desirably, the alkanols undergoing photochlorination in accordance with the practices of this invention have a carbon chain length, $C_4$ and higher and an hydroxyl substitution, such that the alkanol is capable of undergoing δ-chlorination with the result that by employing the photochlorination process in accordance with this invention, δ-chlorination of the alkanol is selectively or predominantly achieved in the substantial absence of or with a substantial reduction in competing reactions (oxidation and chlorination).

The practices of this invention are particularly applicable to the photochlorination of cyclopentanol which undergoes photochlorination in accordance with the chemical reaction,

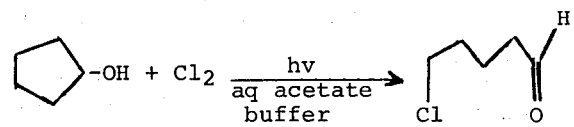

with the quantitative production of 5-chloropentanal.

As indicated hereinbefore, the alkanols, primary and secondary alkanols, which are usefully employed in the practices of this invention are the $C_4$ and higher carbon chain length alkanols, such as the $C_4$-$C_{18}$ alkanols. The alkanols which are usefully chlorinated in accordance with this invention include not only the aliphatic, straight chain and branched chain, $C_4$ and higher alkanols but also the cycloaliphatic $C_4$ and higher alkanols, such as the $C_4$-$C_{12}$ cycloalkanols. Alkanols which are usefully photochlorinated in accordance with the practices of this invention include 1-butanol, 1-pentanol, 2-pentanol, 1-hexanol, 2-hexanol, 1-heptanol, 2-heptanol, 1-octanol, 2-octanol and the higher straight chain or non-straight chain alkanols, including the monohydroxy or polyhydroxy-substituted alkanols. The cycloaliphatic or cycloalkanols usefully photochlorinated include the $C_4$-$C_{12}$ cycloaliphatic alcohols, particularly the unsubstituted, monohydroxy cycloalkanols, such as cyclohexanol, cyclooctanol, cyclodecanol and cyclododecanol. Cyclopentanol is of special interest in accordance with the practices of this invention since cyclopentanol undergoes photochlorination quantitatively to yield 5-chloropentanal.

The photochlorination reaction is carried out by introducing gaseous chlorine into contact with the reaction mixture containing the alkanol and the aqueous buffered solvent. The gaseous chlorine might be introduced thereinto by volatilization of liquid chlorine from a separate source or might be introduced into the reaction mixture in a gaseous stream admixed with nitrogen, the nitrogen serving as a carrier for the chlorine and also serving to blanket the reaction mixture with an inert nitrogen atmosphere, thereby excluding oxygen from contact with the reaction mixture. The photochlorination reaction is carried out while the reaction mixture is stirred and while the reaction mixture is irradiated, such as with a suitable light source, e.g. visible light source, as might be provided by a 300-W tungsten bulb. Usually, the addition of the gaseous chlorine is accomplished in a matter of minutes up to about 1–2 hours, more or less, while stirring and irradiating the reaction mixture. Upon completion of the reaction, i.e., when the required or desired stoichiometric amount of chlorine has been added to the reaction mixture and when testing of the reaction mixture indicates that the reaction is completed as indicated by a KI test, the resulting reaction mixture is then extracted with a suitable solvent for the recovery of the chlorinated alkanol.

blanket of gaseous nitrogen with stirring and 0.5 Equiv. of $Cl_2$ yielded products which analyzed as set forth in accompanying Table I:

TABLE I

| | Photochlorination of Alcohols (0.90 M) in Aqueous Acetate Buffer (4.7 M, pH 5) at 25° under $N_2$ with Stirring and 0.5 Equiv of $Cl_2$ | | | | | | | |
|---|---|---|---|---|---|---|---|---|
| | Relative gc band areas, % | | | | | | | |
| Alcohol | 1-Cl | 2-Cl | 3-Cl | 4-Cl | 5-Cl | 6-Cl | RCOOR | Ketone |
| 1-Butanol | | 20 | 30 | 50 | | | 0 | |
| 1-Hexanol | | 1 | 4 | 77 | 8 | 0 | 10 | |
| 2-Pentanol[a] | 5 | | 6 | 21 | 53 | | | 16 |
| 2-Octanol[a] | 0 | | 0 | 8 | 83 | 3[b] | | 0 |

[a]In the absence of irradiation, the products were 50% recovered alcohols, 48% ketone, and ~2% chloroketones.
[b]No gc bands could be detected in the region expected for the 7-Cl and 8-Cl derivatives.

Additional details on how the reactions in accordance with this invention are carried out are set forth in our co-authored publication entitled "Photochlorination of Alcohols," Journal of Organic Chemistry, 39, 520–523 (1974). The disclosures of this publication are herein incorporated and made part of this disclosure.

Experiments demonstrating the practices of this invention and the results obtainable have been carried out. In these experiments the alkanol (0.15 mol) was added to 150 ml of an aqueous acetate buffer prepared by dissolving 408 grams of sodium acetate trihydrate and 102 grams of acetic acid in water and diluting to 1 liter. While the reaction mixture containing the alkanol and the aqueous acetate butter was magnetically stirred and while it was irradiated with a 300-W tungsten bulb equipped with a parallel reflector, 0.07 mol of weighed liquid $Cl_2$ was allowed to vaporize into the reaction vessel into contact with the reaction mixture. The chlorine addition required about 20 minutes and stirring and irradiation was continued until a KI test on the sample of the resulting reaction mixture was negative. The resulting reaction mixture was extracted with diethyl ether and the extract washed with 5 percent $Na_2CO_3$ and dried over $MgSO_4$. The solvent was removed by aspiration.

Analysis of the reaction products of the photochlorination of 1-pentanol (0.90 M) with chlorine at 25°C. under a blanket of gaseous nitrogen showed there was obtained (relative yield at 50 percent conversion) 0 percent 2-Cl, 9 percent 3-Cl, 86 percent δ-chlorinated or 4-Cl, 1 percent 5-Cl and 4 percent pentyl pentanoate. With respect to the photochlorination of 2-hexanol (0.90 M) with $Cl_2$ at 25°C. under a blanket of gaseous nitrogen analysis indicates there was obtained, based on relative yields at 50 percent conversion, 3 percent 3-Cl, 5 percent 4-Cl, 75 percent 5-Cl or the δ-chlorinated hexanol, 5 percent 6-Cl, 12 percent 2-hexanone and 0 percent chloro-2-hexanones.

The photochlorination of other alcohols (0.90 M) in aqueous acetate buffer (4.7 M, pH 5) at 25°C. under a The photochlorination of the cycloalkanol, cyclopentanol, which represents the preferred embodiment of the practices of this invention, for the production of 5-chloropentanal quantitatively was carried out in accordance with the following procedure. A mixture of 17.6 grams (0.200 mol) of cyclopentanol and 200 ml of aqueous acetate buffer prepared as described hereinabove was introduced into a 500 ml flask equipped with a dry ice-acetone condenser and a cooling bath at 15°C. After sweeping with gaseous nitrogen, 17.8 grams (0.250 mol) of gaseous chlorine was introduced over 30 minutes with stirring and irradiation (300-W tungsten sunlamp). Stirring and irradiation was continued until a KI test for $Cl_2$ was negative (1–2 hours). During the reaction a slow stream of gaseous nitrogen was maintained and this accounts for the loss of some chlorine.

The resulting reaction mixture was extracted with diethyl ether. The extract was washed with 5 percent $Na_2CO_3$, dried over $MgSO_4$ and concentrated under vacuum to give 22.2 grams of ether-free product. The nmr spectrum in $CCl_4$ indicated 80 percent 5-chloropentanal [$\delta$1.75 (m, 4 H), 2.45 (m, 2 H), 3.55 (t, 2 H) and 9.60 (s, 1 H)] and 20 percent cyclopentanol [$\delta$1.55 (m, 8 H) and 4.20 (m, 1 H)]. A gc analysis of the product and the acetylated product confirmed that only cyclopentanol and 5-chloropentanal were present. The photochlorination of cyclopentanol in accordance with this invention provides an attractive method for the quantitative production of 5-chloropentanal.

The photochlorination technique in accordance with this invention is useful for the production of a wide variety of chlorinated alcohols, particularly the chlorinated n-alkanols, wherein the chlorination is achieved at the delta ($\delta$) position. The chlorinated alkanols and other chlorinated derivatives produced in accordance with the practices of this invention are valuable commercial chemicals and have a very wide variety of uses, such as solvents, particularly selective solvents, chemical intermediates, additives in connection with pesticidal agents, textile treating agents and the like.

As will be apparent to those skilled in the art in the light of the foregoing disclosure, many modifications, alterations and substitutions are possible in the practice of this invention without departing from the spirit or scope thereof.

We claim:
1. A method for the photochlorination of an alkanol which comprises reacting a $C_4$ or higher alkanol in a liquid aqueous buffered solvent at a pH in the range from about 4 to about 9 with chlorine in the substantial absence of oxygen while irradiating the resulting reaction mixture.

2. A method in accordance with claim 1 wherein said aqueous solvent is buffered to a pH in the range about 5–6.

3. A method in accordance with claim 1 wherein the reaction mixture is maintained at a temperature in the range from about 15°C. to about 25°C.

4. A method in accordance with claim 1 wherein the reaction mixture is maintained at substantially ambient temperature.

5. A method in accordance with claim 1 wherein the alkanol is a monohydroxy-substituted alkanol.

6. A method in accordance with claim 1 wherein the alkanol is a $C_4$-$C_{18}$ alkanol.

7. A method in accordance with claim 1 wherein said alkanol is a cycloalkanol.

8. A method in accordance with claim 1 wherein said alkanol is a $C_4$-$C_{12}$ cycloalkanol.

9. A method in accordance with claim 1 wherein said alkanol has a carbon chain length and hydroxyl group substitution to permit δ-chlorination of said alkanol.

10. A method in accordance with claim 1 wherein said alkanol is 1-butanol.

11. A method in accordance with claim 1 wherein said alkanol is 1-pentanol.

12. A method in accordance with claim 1 wherein said alkanol is 2-pentanol.

13. A method in accordance with claim 1 wherein said alkanol is 1-hexanol.

14. A method in accordance with claim 1 wherein said alkanol is 2-hexanol.

15. A method in accordance with claim 1 wherein said alkanol is 1-octanol.

16. A method in accordance with claim 1 wherein said alkanol is 2-octanol.

17. A method in accordance with claim 1 wherein said alkanol is cyclopentanol.

18. A method in accordance with claim 17 wherein said aqueous buffered solvent is an aqueous acetate buffer solvent at a pH of about 4–6.

19. A method for the production of 5-chloropentanal involving the photochlorination of cyclopentanol which comprises forming a reaction mixture comprising cyclopentanol in a liquid aqueous buffered solvent at a pH in the range 4–6, introducing with stirring chlorine into the reaction mixture in the substantial absence of oxygen while irradiating the resulting reaction mixture and recovering 5-chlorpentanol as product from the resulting reaction mixture.

20. A method in accordance with claim 19 wherein said reaction mixture is maintained during photochlorination at a temperature in the range about 10°–35°C.

21. A method in accordance with claim 19 wherein said aqueous buffered solvent is an aqueous acetate buffer solvent at a pH of about 5.

22. A method in accordancne with claim 19 wherein 5-chloropentanal is recovered as product from the resulting reaction mixture by solvent extraction.

23. A method in accordance with claim 22 wherein the solvent employed for the solvent extraction for 5-chloropentanal from said resulting reaction mixture is diethyl ether.

* * * * *